United States Patent [19]

Pross et al.

[11] 4,449,537

[45] May 22, 1984

[54] RESPIRATION MONITOR

[75] Inventors: Gerhard Pross, Weil im Schönbuch; Frank Rochlitzer, Altdorf, both of Fed. Rep. of Germany

[73] Assignee: Hewlett-Packard GmbH, Boblingen, Fed. Rep. of Germany

[21] Appl. No.: 355,961

[22] Filed: Mar. 8, 1982

[51] Int. Cl.³ .............................................. A61B 5/05
[52] U.S. Cl. .................................................. 128/723
[58] Field of Search .......................... 128/716, 720–724

[56] References Cited

U.S. PATENT DOCUMENTS

| | | | |
|---|---|---|---|
| 3,976,052 | 8/1976 | Junginger et al. | 128/723 |
| 4,306,567 | 12/1981 | Krasner | 128/721 X |
| 4,379,460 | 4/1983 | Judell | 128/723 X |

FOREIGN PATENT DOCUMENTS

| | | |
|---|---|---|
| 1766759 | 2/1972 | Fed. Rep. of Germany . |
| 2418910 | 10/1975 | Fed. Rep. of Germany . |
| 2527475 | 12/1976 | Fed. Rep. of Germany . |
| 1575190 | 6/1969 | France . |
| 2267734 | 11/1975 | France . |

*Primary Examiner*—Lee S. Cohen
*Attorney, Agent, or Firm*—Stephen P. Fox

[57] ABSTRACT

A respiration monitor for detecting effective respiration of a patient includes circuitry for suppressing the indication of unwanted signals due to heart activity, noise and flat breathing. A first threshold circuit is provided for increasing the sensitivity of the respiration monitor in response to a decreasing amplitude of the measured respiration signals. A first comparator circuit provides a fixed amplitude threshold below which detected signals are fully neglected. A second threshold circuit provides an adjustable amplitude threshold for the measured respiration signal, which threshold is raised in response to a decreasing respiration frequency below a predetermined frequency limit. Effective respiration is indicated only if all the aforementioned amplitude thresholds are exceeded.

9 Claims, 1 Drawing Figure

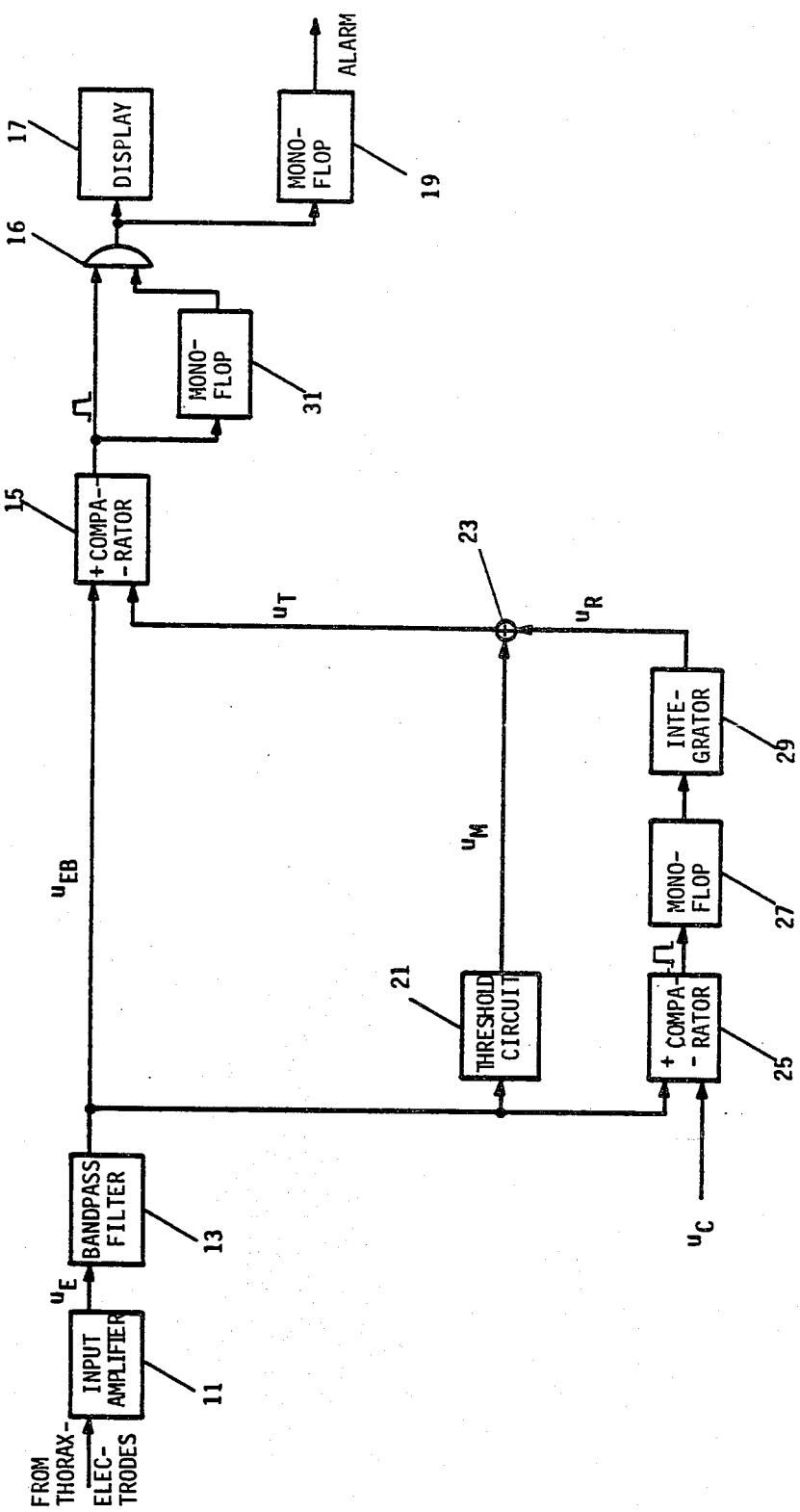

RESPIRATION MONITOR

BACKGROUND OF THE INVENTION

This invention relates to a respiration monitor, in which the respiration activity is monitored by measuring the variations of the thorax impedance or other suitable parameters of a patient caused by his respiration activity.

A sufficient gas exchange in the lung is assured only if the lung is sufficiently ventilated. This ventilation is dependent on the respiration frequency on the one hand and on the respiration "deepness" (breath volume) on the other hand. Respiration monitors are used for monitoring the respiration of patients exposed to danger, e.g., patients in intensive care stations or prematurely born children. Generally, such instruments register the respiration activity and produce an alarm signal in the case of cessation of respiration (apnea), if the apnea duration exceeds a predetermined alarm limit.

In most cases the respiration monitoring is based on an impedance measurement of the patient's thorax. However, other measuring methods are also known, e.g., measuring the temperature variations of the respiration air or pressure variations between body and support.

Effective respiration is possible with relatively low frequency and deep breathing as well as with relatively high frequency and flatter breathing. Some prior art respiration monitors comprise an automatic sensitivity control responsive to the amplitude of the respiration signals. This control is performed with a given delay corresponding to a given time constant. In order to prevent misinterpretation of noise and artifacts as respiration signals, a minimum amplitude threshold is provided, below which respiration signals are no longer detected. If this threshold is not reached for a duration exceeding the alarm limit an alarm signal is produced.

Since the minimum amplitude threshold must be so low that all effective breaths are detected, it may happen that spurious signals exceed this threshold and are misinterpreted as respiration signals although a possible apnea is present. Such spurious signals may have their origin in the heart activity, for example. A respiration monitor capable of suppressing such spurious signals is described in U.S. Pat. No. 3,976,052, issued to Gerhard Junginger and Helmut Zeeb and assigned to the assignee of this application. The respiration monitor described in this patent operates with two amplitude thresholds, one of which is a fixed minimum threshold and the other one of which is a variable threshold dependent on the respiration amplitude. The respiration monitor is connected to separately receive signals corresponding to the heart beat rate and compare the periods of these signals to the periods of the signals measured at the thorax of the patient. If the periods of both signals are substantially equal, the signals measured at the thorax are actually due to heart activity rather than to respiration. In this case, the variable threshold is raised so that the monitor no longer responds to heart beat related signals but indicates that no respiration signals are measured.

Although capable of good suppression of spurious signals, prior art respiration monitors do not take into account the fact that certain further conditions must be met in order to assure a gas exchange that is sufficient for the patient. For example, if the respiration frequency is low, a predetermined minimum deepness of breath must be achieved.

SUMMARY OF THE INVENTION

It is an object of the present invention to provide a respiration monitor which safely indicates a complete apnea as well as an insufficient respiration.

According to the illustrated embodiment of the invention, the variable amplitude threshold is initially set to a minimum threshold. However, if the breathing space has a long duration, this threshold is raised since a longer breathing space indicates a lower respiration frequency. If insufficient and flat breath occurs with a raised amplitude threshold, no respiration is detected. This condition is handled in the same manner as an apnea. The only breath regarded as effective respiration is a deep breath having a signal amplitude which must be higher and higher as the time interval from the last detected breath increases.

According to a preferred embodiment of the invention, raising of the amplitude threshold can also be implemented with higher respiration frequencies. This assures that only an effective respiration is detected in the higher frequency range where otherwise only a dead volume may oscillate within the patient's respiratory organs.

BRIEF DESCRIPTION OF THE DRAWINGS

The single FIGURE shows a block diagram of the preferred embodiment of the invention.

DESCRIPTION OF THE PREFERRED EMBODIMENT

Thorax electrodes (not shown in the drawing) are connected to a conventional input amplifier 11, the defined output signal of which is 2.35 mV/$\Delta 1 \Omega$. The voltage of this output signal is $u_E$ and is proportional to the delta variation of the thorax impedance, rather than to the absolute thorax impedance, as indicated by the term $\Delta 1 \Omega$. The signal voltage $u_E$ is applied to a band-pass filter 13 having a lower frequency limit of 0.2 Hz (corresponding to 12 breaths per minute) and an upper frequency limit of 2 Hz (120 breaths per minute), for example. The band-pass characteristic causes an attenuation of signals with frequencies outside said frequency limits since they are not relevant for respiration monitoring. Band-pass filter 13 additionally has a voltage gain of 426 leading to an output voltage $u_{EB}$ of 1 V/$\Delta 1 \Omega$ in the pass-band.

The output voltage $u_{EB}$ of band-pass filter 13 is applied to the positive input of a comparator 15. The negative input of comparator 15 receives a trigger threshold voltage $u_T$ generated in the manner as described hereinafter. Comparator 15 generates a pulse at its output every time the peak-to-peak amplitude of voltage $u_{EB}$ is higher than threshold voltage $u_T$. These pulses each indicate an effective breath and can be post-processed, e.g., in a display unit 17. Additionally, they are applied to a re-triggerable monoflop 19, the delay time of which corresponds to a pre-determined alarm limit. If the pulse period is shorter than said alarm limit, e.g., 30 seconds, the output signal of monoflop 19 maintains its state excited by its input signal. This state indicates that respiration is effective. If, however, the alarm limit is exceeded, monoflop 19 goes to its basic state. This state is indicated as an alarm or in another suitable manner. The output pulses of comparator 15 are passed to display unit 17 and monoflop 19, respectively, only if they are gated through an AND gate 16 as described hereinafter.

The threshold voltage $u_T$ is produced by an adder 23 as the sum of two threshold voltages $u_M$ and $u_R$. Threshold voltage $u_M$ is supplied by a threshold circuit 21. Threshold circuit 21 generates the threshold voltage $u_M$ as a predetermined fraction, e.g., 60% of the peak-to-peak amplitude of the filtered signal voltage $u_{EB}$. Threshold circuit 21 is known per se (e.g., see U.S. Pat. No. 3,976,052) and can additionally raise the threshold $u_M$ if the frequency of the signal voltage $u_{EB}$ equals the heart beat frequency of the patient. In the described embodiment a first threshold circuit 21 delivers a minimum threshold voltage of 100 mV, corresponding to an impedance variation of 100 milliohms. Other threshold voltages in the range from 100 to 300 mV corresponding to an impedance variation between 100 and 300 milliohms are also suitable.

The filtered signal voltage $u_{EB}$ is additionally applied to the positive input of a comparator circuit comprising comparator 25. The negative input of comparator 25 receives a fixed threshold voltage $u_C$ which in the described embodiment is 80 mV corresponding to a thorax impedance variation of 80 milliohms. This is the given absolute minimum limit for further processing of the respiration signals. Comparator 25 generates at its output a pulse only if the peak-to-peak amplitude of $u_{EB}$ is higher than $u_C$.

The output pulses of comparator 25 are applied to a threshold circuit including a re-triggerable monoflop 27 and an integrator 29. The time delay of monoflop 27 is 2.2 seconds in the described embodiment. This corresponds to the period at a respiration frequency of about 27 breaths per minute. The output signal of monoflop 27 is zero as long as the time intervals between succeeding output pulses from comparator 25 do not exceed 2.2 seconds. If this time interval is exceeded, the output signal of monoflop 27 goes to a positive value for the duration of the pulse from comparator 25.

The output signal of monoflop 27 is applied to an integrator 29. The output voltage of integrator 29 either remains at 80 mV (corresponding to $u_C$), or goes to 80 mV if its input signal is zero, at a rate corresponding to its integration speed. However, positive output signals of monoflop 27 cause raising of the output voltage $u_R$ at a rate corresponding to its integration speed. The longer the duration of a positive output signal of monoflop 27 (i.e., the longer the time delay of 2.2 seconds is exceeded), the higher becomes the output $u_R$ of integrator 29. However, there is provided an upper limit of $u_R = 1.8$ V. The integration speed is 180 mV/sec with an increasing voltage $u_R$ and 450 mV/sec with a decreasing voltage $u_R$, i.e., 2.5 times the integration speed with increasing voltage.

Since voltage $u_R$ is part of the summed threshold voltage $u_T$, the sensitivity threshold of comparator 15 is raised accordingly, when $u_R$ is raised. The higher threshold voltage $u_T$ becomes, the higher must be the peak-to-peak amplitude of $u_{EB}$, i.e., the deeper must be the actual breath, to cause the comparator 15 to produce an output pulse. By this means it is avoided that after an apnea a flat and ineffective respiration or a spurious signal caused by muscle movement would be sufficient to disable the generation of an alarm signal.

Apart from threshold circuit 21 in the described embodiment, the trigger threshold characteristic is substantially determined by two circuits dependent on the respiration frequency, namely band-pass filter 13 on the one hand and the path consisting of comparator 25, monoflop 27 and integrator 29 on the other hand.

Apart from the filter characteristic of band-pass-filter 13 no other upper respiration frequency limit is provided in the respiration monitor so far described. By means of a re-triggerable monoflop 31 a suppression of output signals of comparator 15 above a predetermined frequency limit, for example 200 per minute, can be achieved. Such signals in fact do not indicate an effective respiration. Monoflop 31 is triggered by the trailing edge of each output pulse of comparator 15. If the time between pulses comprising the output signal of comparator 15 is less than 300 milliseconds, the output signal of monoflop 31 remains zero and the AND gate 16 is then disabled. However, if the time between pulses is more than 300 milliseconds, the output signal of monoflop 31 goes to a logic one state before comparator 15 produces its subsequent pulse which then can pass AND gate 16.

We claim:

1. Apparatus for monitoring the respiration activity of a patient and for suppressing disturbing and spurious signals comprising:
   respiration detector means connectable to a patient for providing a variable respiration signal corresponding to the patient's respiration activity;
   first threshold circuit means coupled to said respiration detector means for producing an amplitude threshold decreasing at most to a given minimum value in response to a decreasing amplitude of said variable respiration signal;
   first comparator means coupled to receive said variable respiration signal and a fixed amplitude threshold for suppressing said variable respiration signal below said fixed amplitude threshold;
   second threshold circuit means receiving the output of said first comparator means and coupled to raise said amplitude threshold if the frequency of said variable respiration signal decreases below a predetermined frequency limit; and
   second comparator means coupled to said respiration detector means and said first and second threshold circuit means for producing a valid respiration indication in response to said variable respiration signal only if said variable respiration signal exceeds said amplitude threshold produced, in combination, by said first and second threshold circuit means.

2. Apparatus as set forth in claim 1, wherein said predetermined respiration frequency limit is about 27 breaths per minute.

3. Apparatus as set forth in claim 1, further comprising a band-pass filter connected to said respiration detector means, delivering said variable respiration signal to said first and second comparator means and said first threshold circuit means, said band-pass filter having the lower and upper frequency limits corresponding to the limits of a frequency range relevant to evaluation of the respiration activity.

4. Apparatus as set forth in claim 3, wherein said lower frequency limit of said band-pass filter is about 0.2 Hz and said upper frequency limit is about 2 Hz.

5. Apparatus as set forth in claim 1, further including respiration frequency limit detector means coupled to said second comparator means and being capable of fully suppressing said valid respiration indication beyond a predetermined absolute frequency limit.

6. Apparatus as set forth in claim 5, wherein said absolute frequency limit is about 200 breaths per minute.

7. Apparatus as set forth in claim 1, wherein said respiration detector means monitors respiration activity by measuring the thorax impedance variations of the patient and wherein said minimum value produced by said first threshold circuit means corresponds to an impedance variation between 100 and 300 milliohms.

8. Apparatus as set forth in claim 1, wherein said second threshold circuit means comprises integrator means for raising said amplitude threshold at a first integration speed during time intervals exceeding the period duration corresponding to said predetermined frequency limit, and for lowering said amplitude threshold at a second integration speed during the remaining time intervals.

9. Apparatus as set forth in claim 8, wherein said first integration speed substantially corresponds to a variation by said minimum value per second and that said second integration speed substantially corresponds to a variation by 2.5 times said minimum value per second.

* * * * *